（12）United States Patent
Lee

US009168009B2

(10) Patent No.: US 9,168,009 B2
(45) Date of Patent: Oct. 27, 2015

(54) FLUOROSCOPY TYPE FOUR-POINT FRAME FOR SPINE SURGERY

(71) Applicant: Chien-Kun Lee, New Taipei (TW)

(72) Inventor: Chien-Kun Lee, New Taipei (TW)

(*) Notice: Subject to any disclaimer, the term of this patent is extended or adjusted under 35 U.S.C. 154(b) by 260 days.

(21) Appl. No.: 13/834,013

(22) Filed: Mar. 15, 2013

(65) Prior Publication Data

US 2014/0100446 A1     Apr. 10, 2014

(30) Foreign Application Priority Data

Oct. 8, 2012   (TW) .............................. 101219460 U (51) Int. Cl.
| | |
|---|---|
| *A61B 5/05* | (2006.01) |
| *A61B 6/04* | (2006.01) |
| *A61B 6/12* | (2006.01) |
| *A61B 19/00* | (2006.01) |
| *A61G 13/12* | (2006.01) |
| *A61B 6/00* | (2006.01) |

(52) U.S. Cl.
CPC .............. *A61B 6/0428* (2013.01); *A61B 6/0442* (2013.01); *A61B 6/12* (2013.01); *A61B 6/52* (2013.01); *A61B 19/5244* (2013.01); *A61G 13/12* (2013.01); *A61G 13/129* (2013.01); *A61B 6/485* (2013.01); *A61G 2200/325* (2013.01)

(58) Field of Classification Search
CPC ........... A61G 13/1285; A61G 13/1225; A61G 13/101; A61G 13/1295; A61G 13/12; A61G 2200/325; A61G 2013/0054; A61B 6/0421; A61B 6/04; A61B 6/0428; A61B 6/12; A61B 6/485; A61B 6/0442; A61B 6/52; A61B 19/5244
USPC .......................................................... 600/424
See application file for complete search history.

(56) References Cited

U.S. PATENT DOCUMENTS

| | | | | |
|---|---|---|---|---|
| 5,197,975 | A * | 3/1993 | Mombrinie | 606/238 |
| 6,023,800 | A * | 2/2000 | Stickley | 5/621 |
| 6,076,525 | A * | 6/2000 | Hoffman | 128/845 |
| 6,154,901 | A * | 12/2000 | Carr | 5/621 |
| 7,143,458 | B2 * | 12/2006 | Slater, Jr. | 5/623 |
| 2006/0242765 | A1 * | 11/2006 | Skripps et al. | 5/621 |
| 2006/0253985 | A1 * | 11/2006 | Skripps | 5/622 |

* cited by examiner

*Primary Examiner* — Bo J Peng
(74) *Attorney, Agent, or Firm* — Guice Patents PLLC (57) ABSTRACT

The present invention relates to a fluoroscopy type four-point frame for spine surgery comprising an upper support plate, two pairs of slide seats, a pair of slide rails and two pairs of support cushions. The left and right side defined at the front and rear of the upper support plate are respectively provided with a pair of the slide seats connected through the slide rail, thereby allowing each of the slide seats to slide towards left and right at the corresponding edge of the upper support plate. The front and rear of the pair of the slide rails are respectively provided with a pair of the support cushions, thereby allowing each of the support cushions to forwardly and backwardly slide on the corresponding slide rail; because the frame for spine surgery is made of a non-metal material, no interference of metal component is generated when spine fluoroscopy is processed.

10 Claims, 7 Drawing Sheets

FLUOROSCOPY TYPE FOUR-POINT FRAME FOR SPINE SURGERY

BACKGROUND OF THE INVENTION

1. Field of the Invention

The present invention relates to a frame for spine surgery, especially to a fluoroscopy type four-point frame for spine surgery.

2. Description of Related Art

A four-point frame for spine surgery is commonly used in the spine surgical operation; when in use, the four-point frame for spine surgery is disposed on an operating table, and the patient lies in the prone position on the frame for spine surgery and supported by two pairs of support cushions correspondingly disposed at two sides.

With the development of surgical technology, many surgeries and diagnosis can be accurately processed through solid photography, so skilled people in the art have invented some fluoroscopy type surgical equipments, e.g. a fluoroscopy type operating table. When in use, the patient lies in the prone position on the fluoroscopy type operating table. The fluoroscopy type operating table allows X-ray to penetrate for providing a full fluoroscopy imaging, but the skeleton of the frame for spine surgery is made of a metal material, such as stainless steel, thereby causing X-ray not being able to penetrate, or even generating interference to the spine imaging, so the full fluoroscopy imaging cannot be carried out.

As such, how to develop a fluoroscopy type four-point frame for spine surgery which can keep the advantages of prior art and allow X-ray to penetrate is an issue to be concerned by skilled people in the art.

SUMMARY OF THE INVENTION

One primary objective of the present invention is to provide a fluoroscopy type four-point frame for spine surgery, in which the left and the right side defined at the front and the rear of an upper support plate are respectively provided with a pair of slide seats connected through a slide rail, thereby allowing each of the slide seats to slide towards left and right at the corresponding edge of the upper support plate so as to adjust the left/right distance of the two pairs of the support cushions for being suitably used in patient having various body shapes. The front and the rear of the pair of the slide rails are respectively provided with a pair of support cushions, thereby allowing each of the support cushions to forwardly and backwardly slide on the corresponding slide rail so as to adjust the front/rear distance of the two pairs of the support cushions for being suitably used in patients having different height, and the support cushions are respectively formed with a fixed inclined angle.

For achieving aforesaid objective, one technical solution of the present invention is to provide a fluoroscopy type four-point frame for spine surgery, which comprises:

an upper support plate, formed as a non-metal plate member allowing X-ray to penetrate, and four corners at the bottom surface are respectively provided with a tubular piece;

two pairs of slide seats, correspondingly disposed at two sides defined at the front and the rear of the upper support plate, each pair of the slide seats is formed with a slide groove sleeved at the front and the rear edge of the upper support plate, and the top surface thereof is screwed with a first rotary button capable of penetrating to the slide groove and locking or releasing the upper support plate thereby adjusting the left/right distance of the two pairs of the slide seats;

a pair of slide rails, respectively combined with each pair of the slide seats disposed at the two sides defined at the front and the rear of the upper support plate; and two pairs of support cushions, each pair of the support cushions are disposed at the front and the rear of each of the slide rails, and each of the support cushions includes a slide rack formed with an engagement groove sleeved with the slide rail, a lateral side of the engagement groove is screwed with a second rotary button capable of locking or releasing the pair of slide rails thereby adjusting the front/rear distance of each pair of the support cushions, wherein the top surface of each of the slide racks is inwardly formed with an inclined surface having a preset inclined angle, and the inclined surface is further combined with a cushion member.

BRIEF DESCRIPTION OF THE DRAWINGS

The present invention will be apparent to those skilled in the art by reading the following detailed description of a preferred embodiment thereof, with reference to the attached drawings, in which.

DETAILED DESCRIPTION OF THE PREFERRED EMBODIMENT

Figure 1:
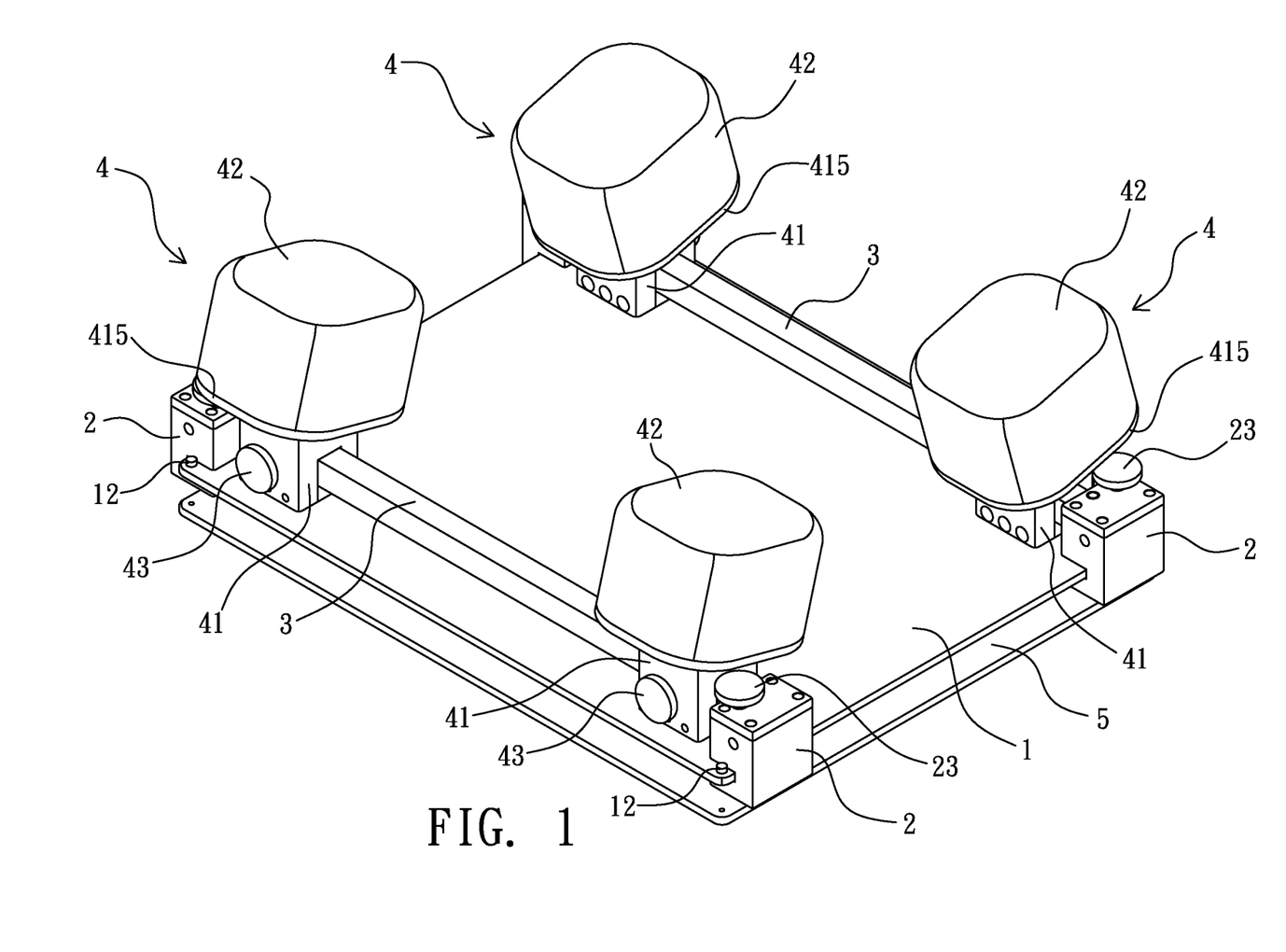
FIG. 1 is a perspective view illustrating the fluoroscopy type four-point frame for spine surgery according to the present invention.
Figure 2:
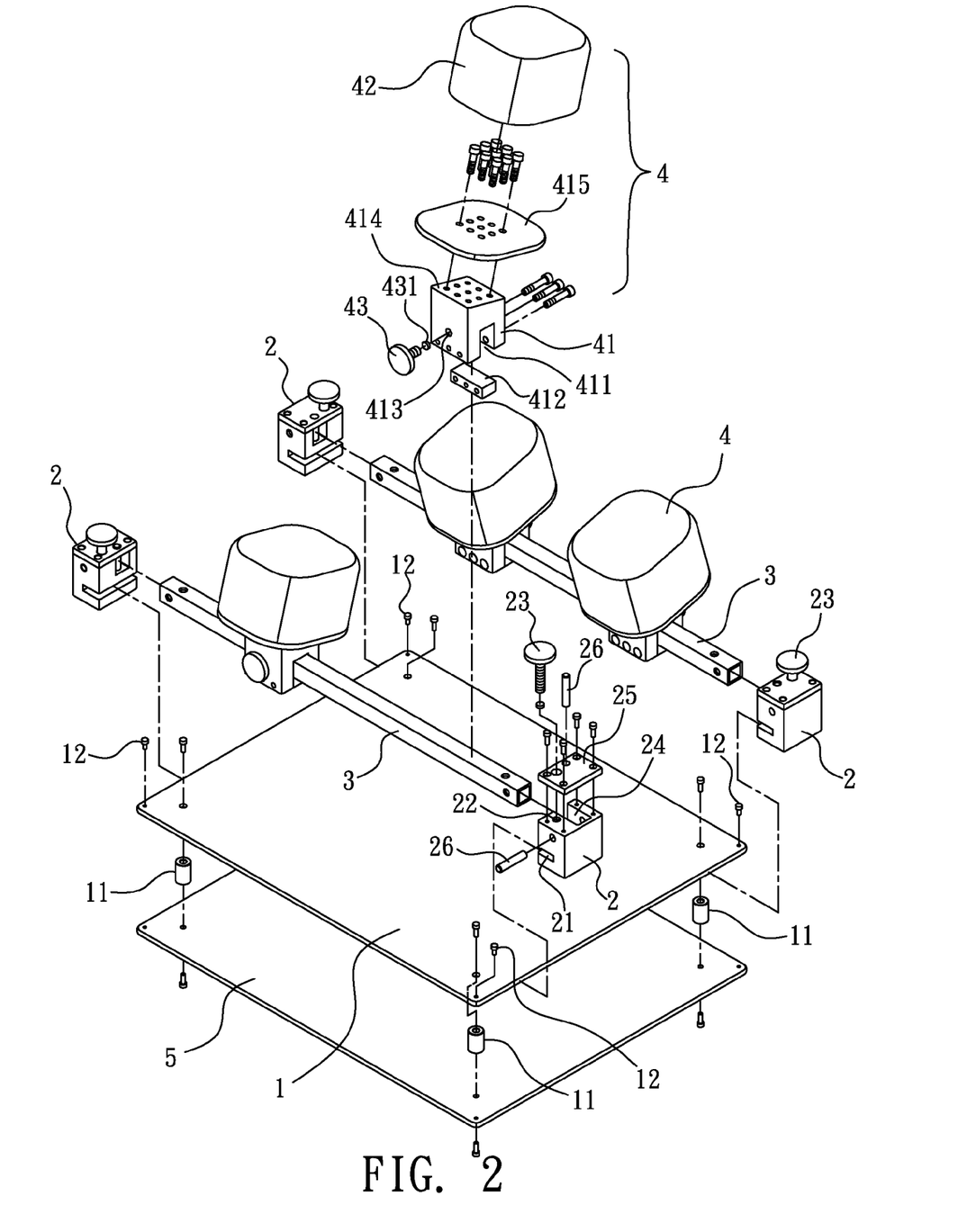
FIG. 2 is a perspective exploded view illustrating the fluoroscopy type four-point frame for spine surgery according to the present invention.
Figure 3:
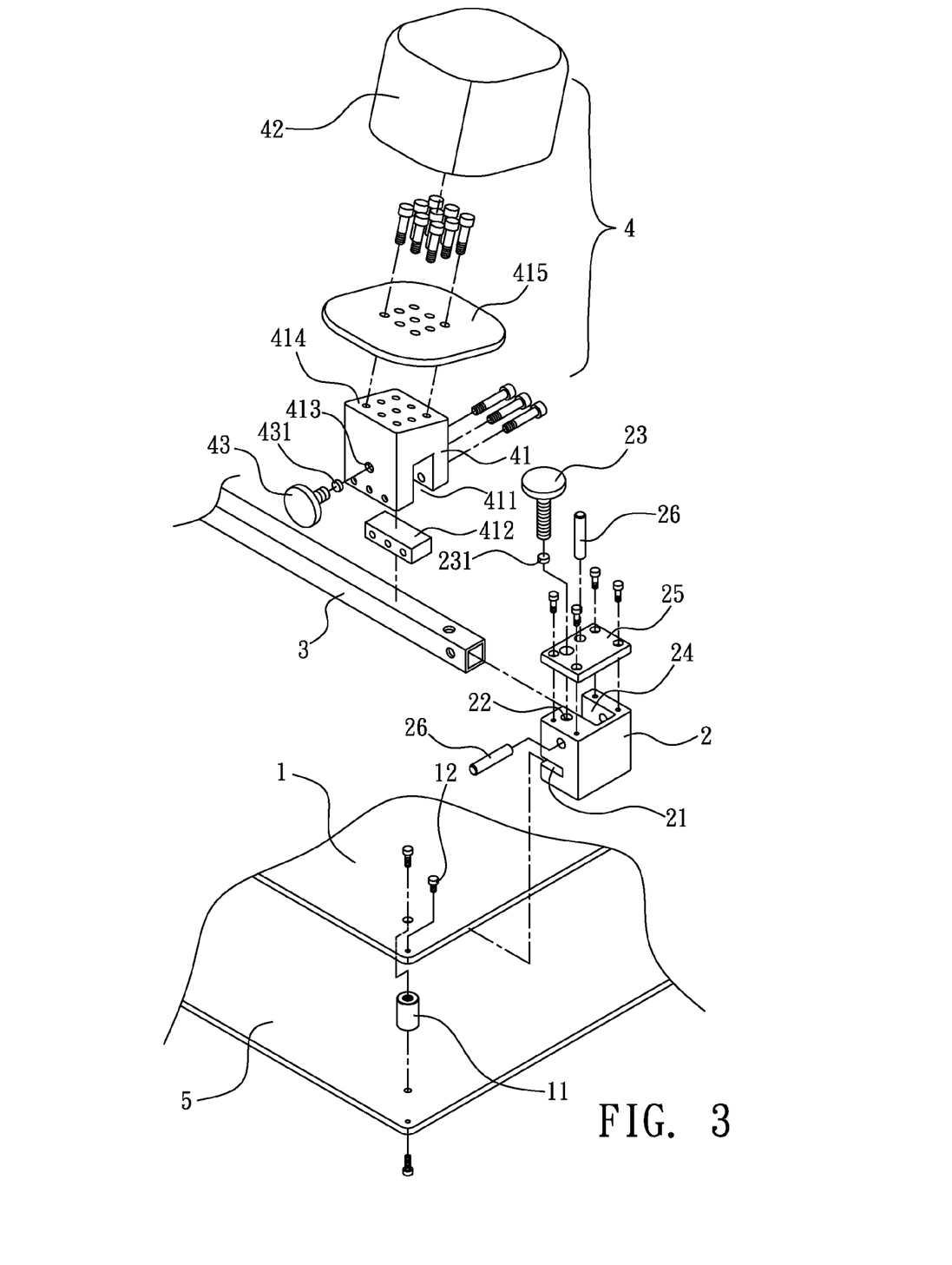
FIG. 3 is a perspective exploded view illustrating the slide seat and the support cushion according to the present invention.
Figure 4A:
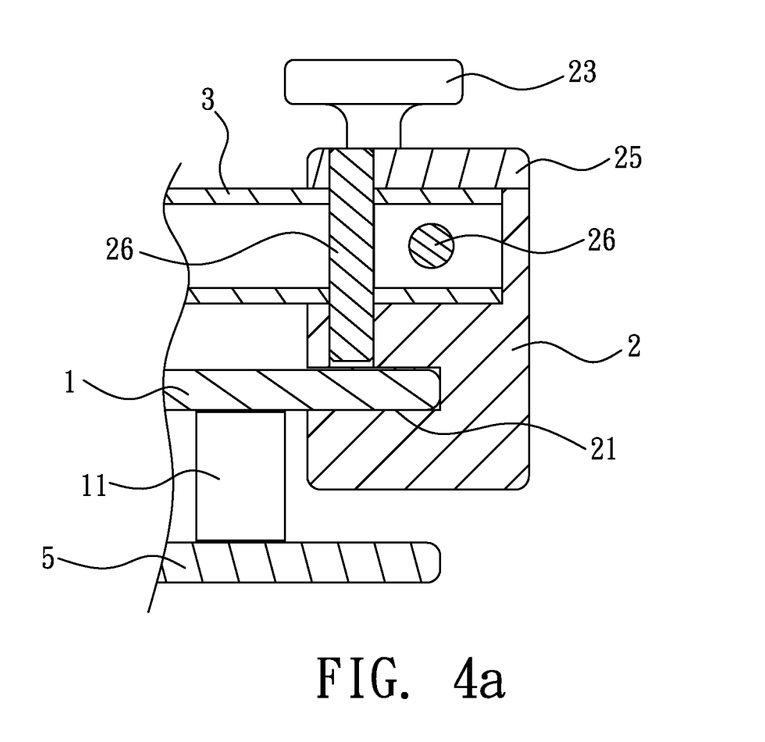
FIG. 4a is a cross sectional view illustrating the assembly of the slide seat according to the present invention.
Figure 4B:
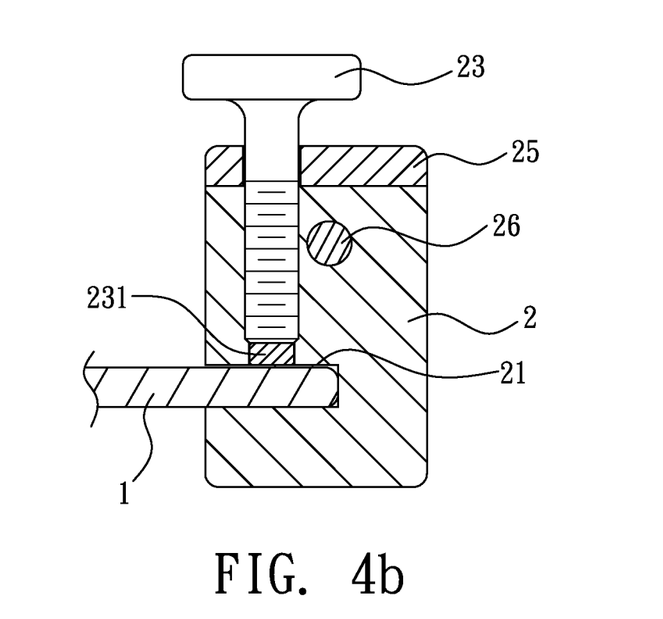
FIG. 4b is another cross sectional view illustrating the assembly of the slide seat taken from another angle according to the present invention.
Figure 5:
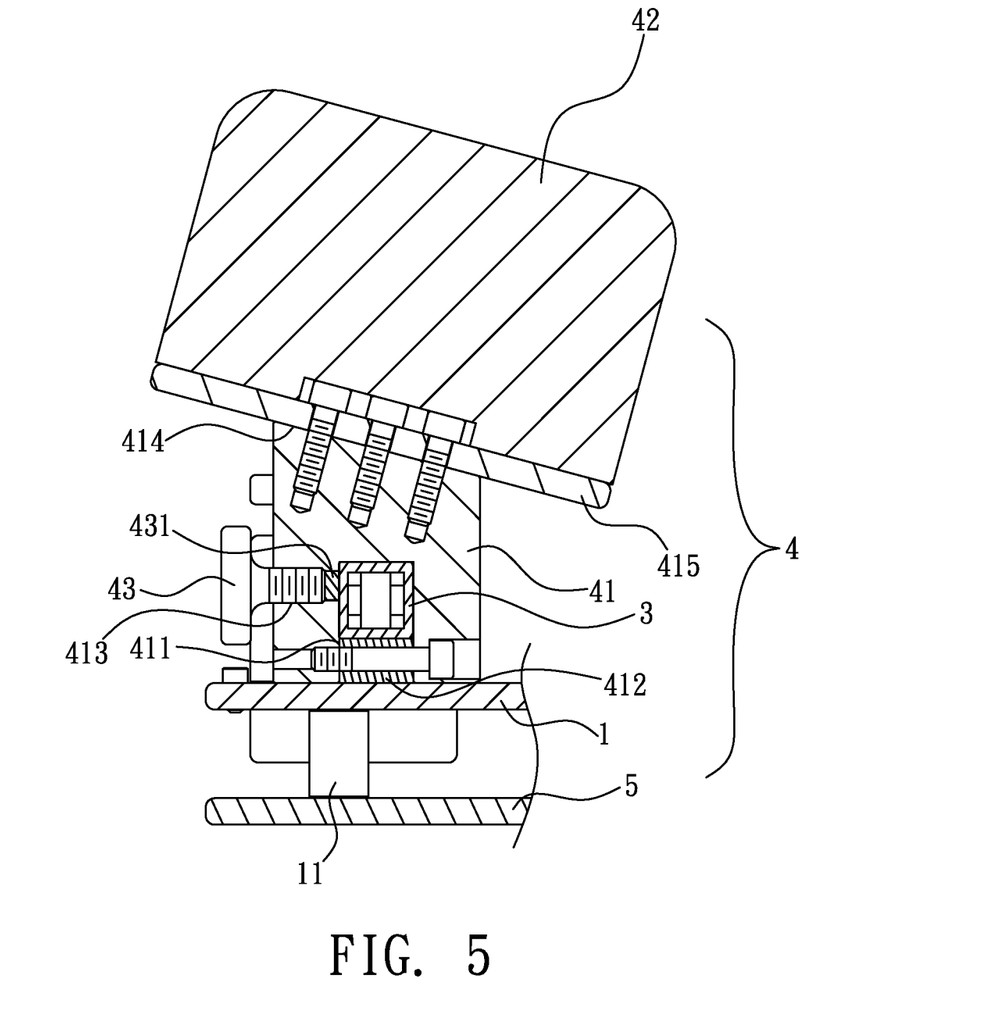
FIG. 5 is a cross sectional view illustrating the assembly of the support cushion according to the present invention.
Figure 6:
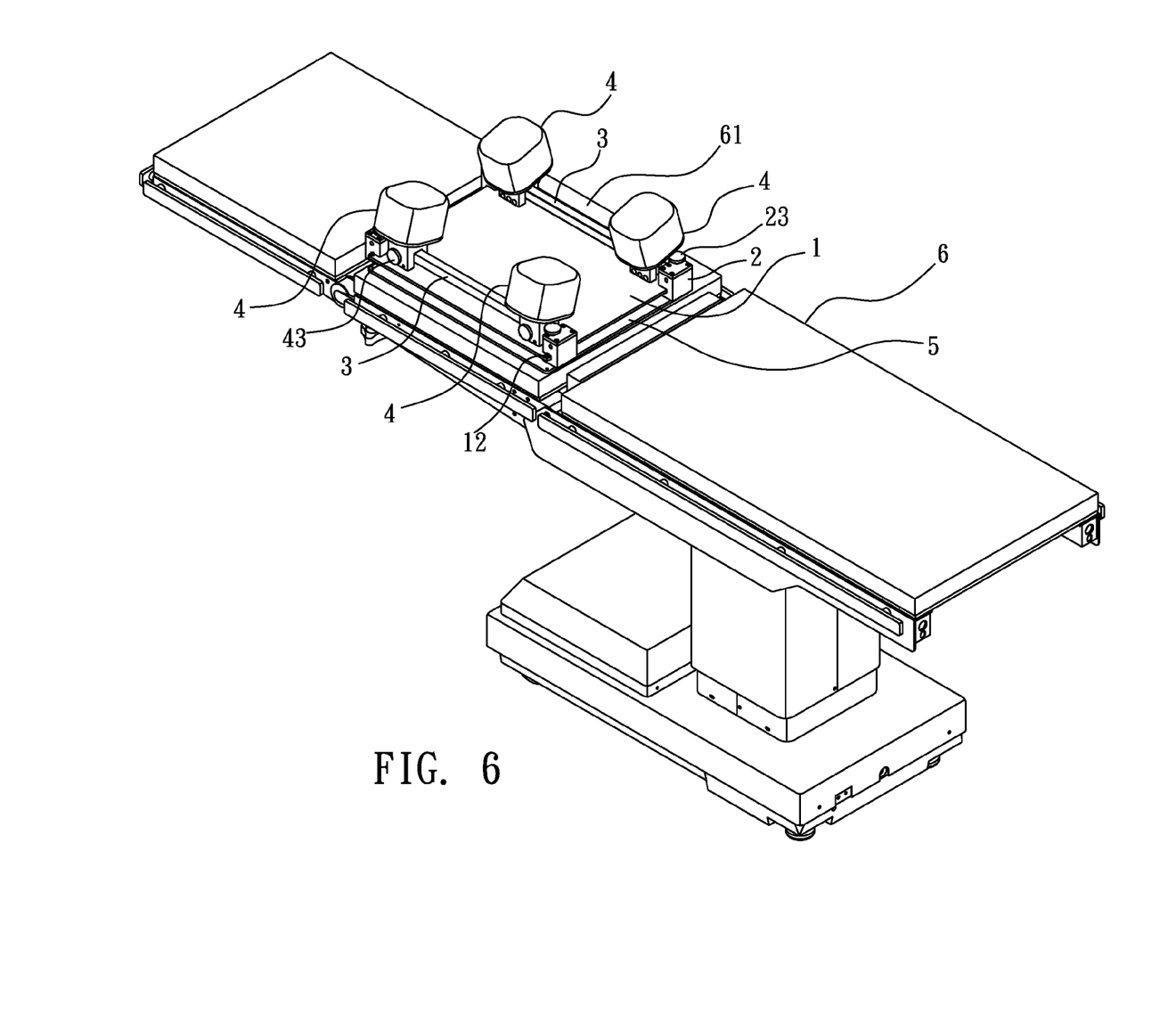
FIG. 6 is a perspective view illustrating the fluoroscopy type four-point frame for spine surgery being disposed on an operating table according to the present invention.
Figure 7:
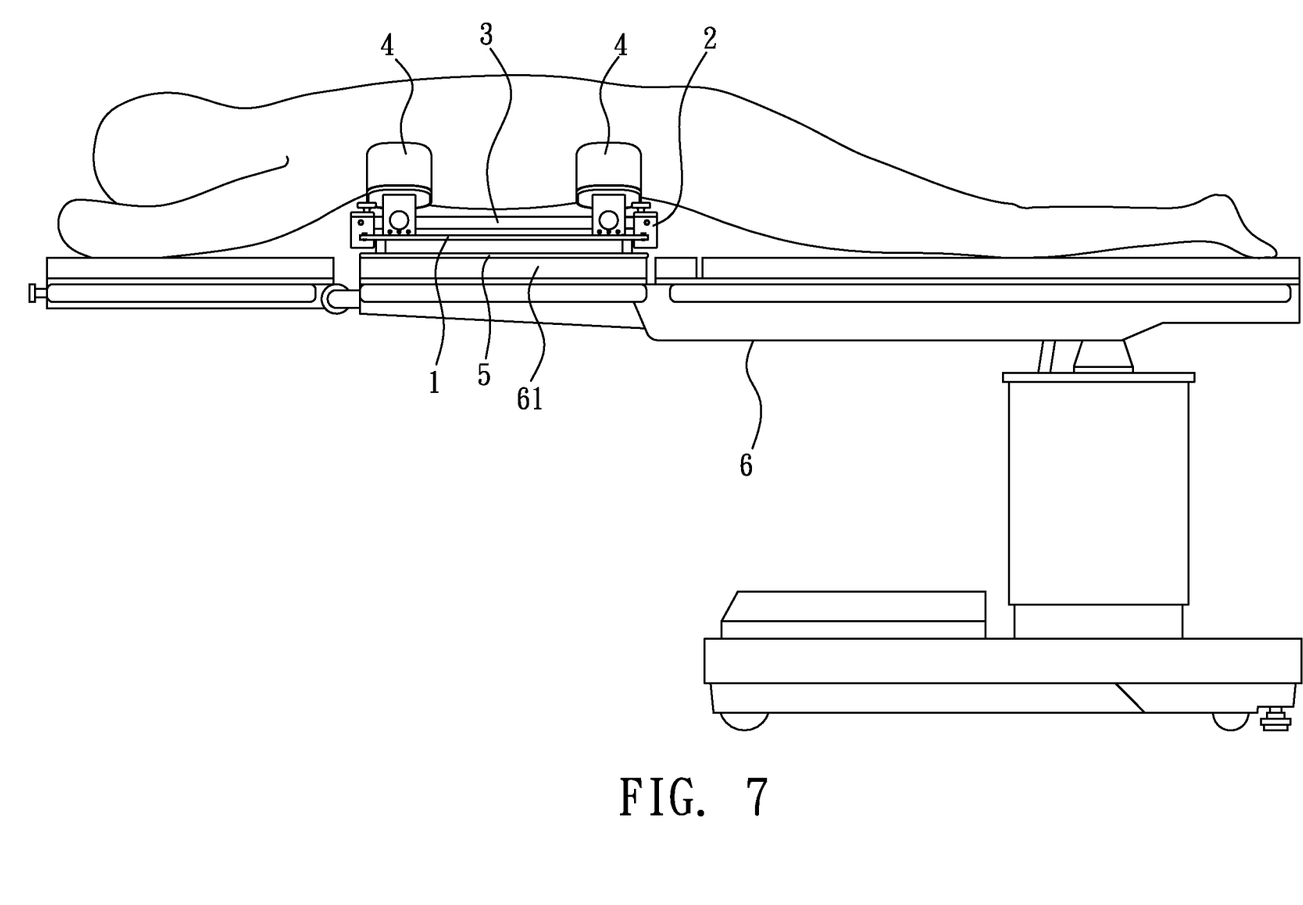
FIG. 7 is a schematic view illustrating the fluoroscopy type four-point frame for spine surgery being disposed on the operating table for processing the X-ray photography according to the present invention.

Referring from FIG. 1 to FIG. 7, wherein FIG. 1 is a perspective view illustrating the fluoroscopy type four-point frame for spine surgery according to the present invention; FIG. 2 is a perspective exploded view illustrating the fluoroscopy type four-point frame for spine surgery according to the present invention; FIG. 3 is a perspective exploded view illustrating the slide seat and the support cushion according to the present invention; FIG. 4a is a cross sectional view illustrating the assembly of the slide seat according to the present invention; FIG. 4b is another cross sectional view illustrating the assembly of the slide seat taken from another angle according to the present invention; FIG. 5 is a cross sectional view illustrating the assembly of the support cushion according to the present invention; FIG. 6 is a perspective view illustrating the fluoroscopy type four-point frame for spine surgery being disposed on an operating table according to the present invention; and FIG. 7 is a schematic view illustrating the fluoroscopy type four-point frame for spine surgery being disposed on the operating table for processing the X-ray photography according to the present invention.

As shown from FIG. 1 to FIG. 5, the fluoroscopy type four-point frame for spine surgery provided by the present invention substantially comprises an upper support plate 1, two pairs of slide seats 2, a pair of slide rails 3, and two pairs of support cushions 4.

The upper support plate 1 is a rectangular non-metal plate member allowing X ray to penetrate, e.g. a carbon fiber plate, a glass fiber plate or a bakelite plate. Four corners of the upper support plate 1 are respectively provided with e.g. a plastic screw passing the upper support plate 1 and screwed with a non-metal tubular piece 11 thereby lifting the upper support plate 1 so as to allow the mentioned slide seats 2 to smoothly slide towards left and right on the upper support plate 1. In addition, the four corners of the upper support plate 1 are further respectively provided with a stop piece 12, e.g. a plastic screw screwed at the four corners of the upper support plate 1, thereby serving as a limitation for the left/right sliding movement of the slide seats 2.

The two pairs of the slide seats 2 are made of a non-metal material, and respectively and correspondingly disposed at two sides defined at the front and the rear (the left and the right side) of the upper support plate 1, as shown from FIG. 2 to FIG. 4b, for providing a clear description, only a pair of slide seats 2 is adopted for illustration. Each pair of the slide seats 2 are formed with a slide groove 21 at the edge facing the upper support plate 1, thereby being able to be disposed at the left and the right side at the front and the rear of the upper support plate 1, the slide seat 2 is longitudinally formed with a screw hole 22 communicated with the slide groove 21, so a first rotary button 23 is enabled to be screwed and abutted against the upper support plate 1 thereby forming packing and positioning. As such, when the first rotary button 23 is loosened, the upper support plate 1 is released through the slide groove 21 and the first rotary button 23, thereby allowing the slide seat 2 to slide towards left and right at the front and the rear of the upper support plate 1 to a preset location, then the first rotary button 23 is tightened, the upper support plate 1 is locked through the first rotary button 23 and the slide groove 21 thereby being positioned. Moreover, for avoiding scratch being generated on the surface of the upper support plate 1 while the first rotary button 23 being tightened, each of the first rotary buttons 23 is provided with a wearing resistant pad 231, e.g. a Teflon pad, between the inner end surface thereof and the surface of the upper support plate 1.

Furthermore, for allowing each pair of the slide seats 2 disposed at the same side to synchronously slide towards left and right on the upper support plate 1, the pair of the slide rails 3 are respectively combined with each pair of the slide seats 2 disposed at two sides at the front and the rear of the upper support plate 1, in other words, the top surface of each pair of the slide seats 2 is combined with one of the slide rails 3, as shown in figures, the pair of the slide rails 3 is made of a non-metal material, e.g. being formed as a pipe member made of carbon fibers, and two end sections thereof are respectively received in accommodation grooves 24 correspondingly formed on each pair of the slide seats 2, and a top cover 25 is provided for sealing the top opening of each of the accommodation grooves 24, thereby the end section of the slide rail 3 being prevented from being longitudinally released from the accommodation groove 24 of each of the slide seats 2. The first rotary button 23 is penetrated the top cover 25 and screwed in the screw hole 22 formed on the top surface of the slide seat 2, thereby enabling the first rotary button 23 to lock or release the upper support plate 1 in the slide groove 21.

In addition, at least a non-metal positioning pin 26 penetrating the slide rail 3 received in the accommodation groove 24 is longitudinally inserted between the top cover 25 and the slide seat 2 at the bottom surface of the slide groove 21, or at least a non-metal positioning pin 26 penetrating the slide rail 3 received in the accommodation groove 24 is transversally inserted in the slide seat 2, thereby enhancing the combing strength of the slide rail 3 and the pair of the slide seats 2. Moreover, the front and the rear of each of the slide rails 3 are installed with one pair of the support cushions 4.

As shown in FIG. 2 and FIG. 5, each of the support cushions 4 is also made of a non-metal material, and includes a slide rack 41 and a cushion member 42. The bottom of the slide rack 41 is formed with an engagement groove 411 sleeved with the slide rail 3, and the bottom opening of the engagement groove 411 is provided, e.g. being screwed, with a bottom cover 412, thereby preventing the slide rack 41 from being longitudinally released from the slide rail 3. The outer side of the slide rack 41 is transversally formed with a screw hole 413 communicated with the engagement groove 411 so as to allow a second rotary button 43 to be screwed and abutted against the slide rail 3 thereby forming packing and positioning. Through tightening or loosening the second rotary button 43, each of the support cushions 4 is enabled to be forwardly/backwardly slide and be positioned on the slide rail 3. Wherein, for avoiding scratch being generated on the surface of the slide rail 3 while the second rotary button 43 being tightened, each of the second rotary buttons 43 is provided with a wearing resistant pad 431, e.g. a Teflon pad, between the inner end surface thereof and the surface of the slide rail 3. In addition, the top surface of the slide rack 41 is inwardly formed with an inclined surface 414 having a preset inclined angle, the inclined angle of the inclined surface 414 is preferably between 10 to 20 degree, and the most favorable inclined angle is 15 degree. Wherein, the inclined surface 414 is further provided with a support sheet 415, the cushion member 42 is disposed on the support sheet 415, thereby allowing each of the cushion members 42 being provided with a fixed inwardly inclined angle relative to the slide rail 3.

Furthermore, the bottoms of the tubular pieces 11 at the four corners defined at the bottom surface of the upper support plate 1 can be further combined with a lower support plate 5, the lower support plate 5 is a rectangular non-metal plate member having the same dimension as the upper support plate 1, the lower support plate 5 can be a carbon fiber plate, a glass fiber plate or a bakelite plate, and a gap is formed between the mentioned two plates, the advantages of having the gap being formed are: the slide seat 2 is allowed to be flexibly adjusted, and a X-ray film to be inserted in the gap for processing X-ray photography.

As shown in FIG. 1, which is a perspective view illustrating the fluoroscopy type four-point frame for spine surgery according to the present invention, the left and the right side at the front and the rear of the upper support plate 1 is respectively sleeved with a pair of the slide seats 2 connected through the slide rail 3, thereby allowing each of the slide seats 2 to slide toward left and right at the edge of the corresponding upper support plate 1, and the left/right distance between the two pairs of the support cushions 4 can be adjusted through the first rotary button 23 of each of the slide seats 3 being tightened and released thereby being suitably used in patients having various body shapes. The front and the rear of the pair of the slide rails 3 are respectively sleeved with the slide racks 41 of the corresponding pair of the support cushions 4, thereby allowing each of the support cushions 4 to forwardly and backwardly slide on the corresponding slide rail 3, and the front/rear distance between the two pair of the support cushions 4 can be adjusted through the second rotary button 43 of each of the slide racks 41 being tightened and released thereby being suitably used in patients having different heights. Moreover, the cushion member 42 of each of the support cushions 4 can be served to provide comfort to a prone position.

Referring to FIG. 1, the upper support plate 1, the slide seats 2, the slide rails 3, the support cushions 4 and the lower support plate 5 are all made of a non-metal material, so no interference would be generated by any metal components while a spine fluoroscopy being processed.

Moreover, after the four corners of the mentioned upper support plate 1 are combined with the tubular pieces 11, the upper support plate 1 is enabled to be directly disposed on a bed plate of an operating table, each of the slide seats 2 is provided with a sufficient moving space as long as the tubular piece 11 is higher than the bottom edge of the slide seat 2, and the whole frame set for spine surgery can be prevented from unintentionally sliding.

As shown in FIG. 6, the fluoroscopy type four-point frame for spine surgery shown in FIG. 1 is directly disposed on a bed plate 61 of a fluoroscopy type operating table 6, and FIG. 7 illustrates a patient lie in the prone position on the four support cushions 4 of the fluoroscopy type four-point frame for spine surgery, so the solid photography, e.g. X-ray photography can be facilitated, thus a spine surgery can be provided with accurate diagnosis and smooth operation.

As what has been disclosed above, the advantages achieved by the present invention are as follows: during the spine surgery, the slide seats, the slide rails and the support cushions of the frame for spine surgery are disposed at two sides of the spine thereby being provided with a larger distance, so when the frame for spine surgery being adopted in the fluoroscopy type operating table and the spine fluoroscopy being desired to be processed, no interference of metal component is generated; moreover, the upper support plate and the lower support plate are made of a fiber plate allowing X-ray to penetrate, so the X-ray fluoroscopy imaging is facilitated, the spine surgery can be provided with accurate diagnosis and smooth operation. Accordingly, the fluoroscopy type four-point frame for spine surgery provided by the present invention is novel and practical in use comparing to prior art.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific examples of the embodiments disclosed and that modifications and other embodiments are intended to be included within the scope of the appended claims. Although specific terms are employed herein, they are used in a generic and descriptive sense only and not for purposes of limitation.

What is claimed is:

1. A fluoroscopy type four-point frame for spine surgery, comprising:
    an upper support plate, two pairs of slide seats, a pair of slide rails, and two pairs of support cushions being made of a non-metal material;
    said upper support plate, formed as a non-metal plate member allowing X-ray to penetrate, and four corners at the bottom surface being respectively provided with a tubular piece;
    said two pairs of slide seats, correspondingly located on two opposing sides defined as a front and a rear of said upper support plate, each slide seat of said two pair of said slide seats having a slide groove and an accommodation groove, the slide groove communicating with a first side, a second side, and a third side of said slide seat and said accommodation groove communicating with said third side and a top of said slide seat, said first side and said third side are located on opposing sides of said slide seat and said second side is located between said first side and said third side, the front and the rear edge of said upper support plate are inserted into a corresponding slide groove of said two pairs of slide seats, and the top surface thereof being screwed with a first rotary button capable of penetrating to said slide groove and locking or releasing said upper support plate thereby adjusting the left/right distance of said two pairs of said slide seats;
    a first end and a second end of each slide rail of said pair of slide rails are inserted into said accommodation groove of a corresponding pair of said slide seats of said two pairs of slide seats respectively; and
    said two pairs of support cushions, each pair of said support cushions being disposed at the front and the rear of each of said slide rails, and each support cushion of said two pair of support cushions including a slide rack having an engagement groove and a bottom cover, each slide rail of said two slide rails is inserted through two corresponding engagement grooves of two support cushions of said two pairs of support cushions, said bottom cover is located in said engagement groove of said slide rack, a bottom of said bottom cover and a bottom of said slide rack are located in a same plane, a lateral side of said engagement groove being screwed with a second rotary button capable of locking or releasing said pair of slide rails thereby adjusting the front/rear distance of each pair of said support cushions, wherein the top surface of each of said slide racks being inwardly formed with an inclined surface having a preset inclined angle, and said inclined surface being further combined with a cushion member.

2. The fluoroscopy type four-point frame for spine surgery as claimed in claim 1, further including a lower support plate, said lower support plate is formed as another non-metal plate member allowing X-ray to penetrate, and combined the bottoms of said tubular pieces at the four corners defined at the bottom surface of said upper support plate, thereby forming a gap between said upper and said lower support plate.

3. The fluoroscopy type four-point frame for spine surgery as claimed in claim 2, wherein said another non-metal plate member is selected from a carbon fiber plate, a glass fiber plate or a bakelite plate.

4. The fluoroscopy type four-point frame for spine surgery as claimed in claim 1, wherein said non-metal plate member is selected from a carbon fiber plate, a glass fiber plate or a bakelite plate.

5. The fluoroscopy type four-point frame for spine surgery as claimed in claim 1, wherein a wearing resistant pad is provided between the inner end surface of said first rotary button and the surface of said upper support plate, a wearing resistant pad is provided between the inner end surface of said second rotary button and the surface of said slide rail.

6. The fluoroscopy type four-point frame for spine surgery as claimed in claim 1, wherein each pair of said slide seats is formed with an accommodation groove allowing end sections of said pair of said slide rails to be received, and the top opening of said accommodation groove is sealed by a top cover; and said first rotary button is penetrated said top cover and screwed in a screw hole formed on the top surface of said slide seat, thereby enabling said first rotary button to lock or release said upper support plate in said slide groove.

7. The fluoroscopy type four-point frame for spine surgery as claimed in claim 6, wherein at least a non-metal positioning pin penetrating said slide rail received in said accommodation groove is longitudinally inserted between said top cover and said slide seat at the bottom surface of said slide groove.

8. The fluoroscopy type four-point frame for spine surgery as claimed in claim 6, wherein at least a non-metal positioning pin penetrating said slide rail received in said accommodation groove is transversely inserted in said slide seat.

9. The fluoroscopy type four-point frame for spine surgery as claimed in claim 1, wherein said inclined angle of said inclined surface is preferably between 10 to 20 degree, and the most favorable inclined angle is 15 degree.

10. The fluoroscopy type four-point frame for spine surgery as claimed in claim 9, wherein said inclined surface is further provided with a support sheet, said cushion member is disposed on said support sheet.

\* \* \* \* \*